(12) United States Patent
van der Maas

(10) Patent No.: US 6,662,626 B2
(45) Date of Patent: Dec. 16, 2003

(54) ASSEMBLY FOR DESORBING SAMPLING TUBES; ADAPTER AND SAMPLING TUBES FOR SUCH AN ASSEMBLY; AND KIT OF PARTS FOR FORMING SUCH AN ASSEMBLY

(75) Inventor: Marinus Frans van der Maas, Arnemuiden (NL)

(73) Assignee: SGT Exploitatie, Middleburg (NL)

( * ) Notice: Subject to any disclaimer, the term of this patent is extended or adjusted under 35 U.S.C. 154(b) by 0 days.

(21) Appl. No.: 10/175,692

(22) Filed: Jun. 20, 2002

(65) Prior Publication Data

US 2002/0157453 A1 Oct. 31, 2002

Related U.S. Application Data

(62) Division of application No. 09/576,407, filed on May 22, 2000.

(30) Foreign Application Priority Data

May 21, 1999 (NL) ............................................. 1012127

(51) Int. Cl.$^7$ ........................ G01N 31/08; G01N 30/04; G01N 30/18
(52) U.S. Cl. ...................... 73/23.35; 73/23.41; 96/105; 422/89; 95/89; 95/82
(58) Field of Search ............................ 73/23.35, 23.41, 73/23.42; 422/89; 95/88, 89, 82; 96/101, 105; 210/656, 668

(56) References Cited

U.S. PATENT DOCUMENTS

| | | | |
|---|---|---|---|
| 3,985,016 A | 10/1976 | Haruki | 23/23.1 |
| 3,996,008 A | 12/1976 | Fine et al. | 23/254 R |
| 4,004,881 A | 1/1977 | Ligon, Jr. | 23/232 C |
| 4,035,168 A | 7/1977 | Jennings | 55/67 |
| 4,422,860 A | 12/1983 | Feinstein | 55/67 |
| 4,470,315 A | 9/1984 | Ellgehausen et al. | 73/863.12 |
| 4,474,588 A | 10/1984 | Hinshaw, Jr. | 55/197 |
| 4,559,063 A | 12/1985 | Munari et al. | 55/67 |
| 4,711,764 A | 12/1987 | Good | 422/65 |
| 4,713,963 A | 12/1987 | Sharp | 73/23.1 |
| 4,864,843 A | 9/1989 | Guieze et al. | 73/23.1 |
| 5,065,614 A | 11/1991 | Hartman et al. | 73/23.35 |
| 5,191,211 A | 3/1993 | Gorman, Jr. | 250/282 |
| 5,281,397 A | 1/1994 | Ligon et al. | 422/89 |
| 5,394,733 A | 3/1995 | Acholla | 73/23.41 |
| 5,472,670 A | 12/1995 | Harrington et al. | 422/89 |
| 5,686,656 A | 11/1997 | Amirav et al. | 73/23.41 |
| 5,711,786 A | 1/1998 | Hinshaw | 95/82 |
| 6,062,065 A | 5/2000 | Sugimoto et al. | 73/23.42 |
| 6,067,402 A | 5/2000 | Kikuchi | 392/386 |
| 6,131,440 A | 10/2000 | Bertrand | 73/23.39 |

FOREIGN PATENT DOCUMENTS

DE 196 53 406 C1 1/1998

*Primary Examiner*—Hezron Williams
*Assistant Examiner*—David J. Wiggins
(74) *Attorney, Agent, or Firm*—Weingarten, Schurgin, Gagnebin & Lebovici LLP

(57) ABSTRACT

An assembly for desorbing sampling tubes comprises a gas chromatograph known per se provided with an injector. The sampling tubes are provided with an inflow opening and an outflow opening. The assembly comprises an adapter which is placed in the injector and which is provided with a chamber which is bounded by a heat conducting housing. The adapter is arranged for placing a sampling tube in the chamber thereof, while in a condition of a sampling tube wherein it is placed in the adapter, the inflow opening thereof is in fluid communication with a first carrier gas supply duct, while the outflow opening of the sampling tube is in fluid communication via the injector with a gas chromatography column disposed in the gas chromatograph.

19 Claims, 10 Drawing Sheets

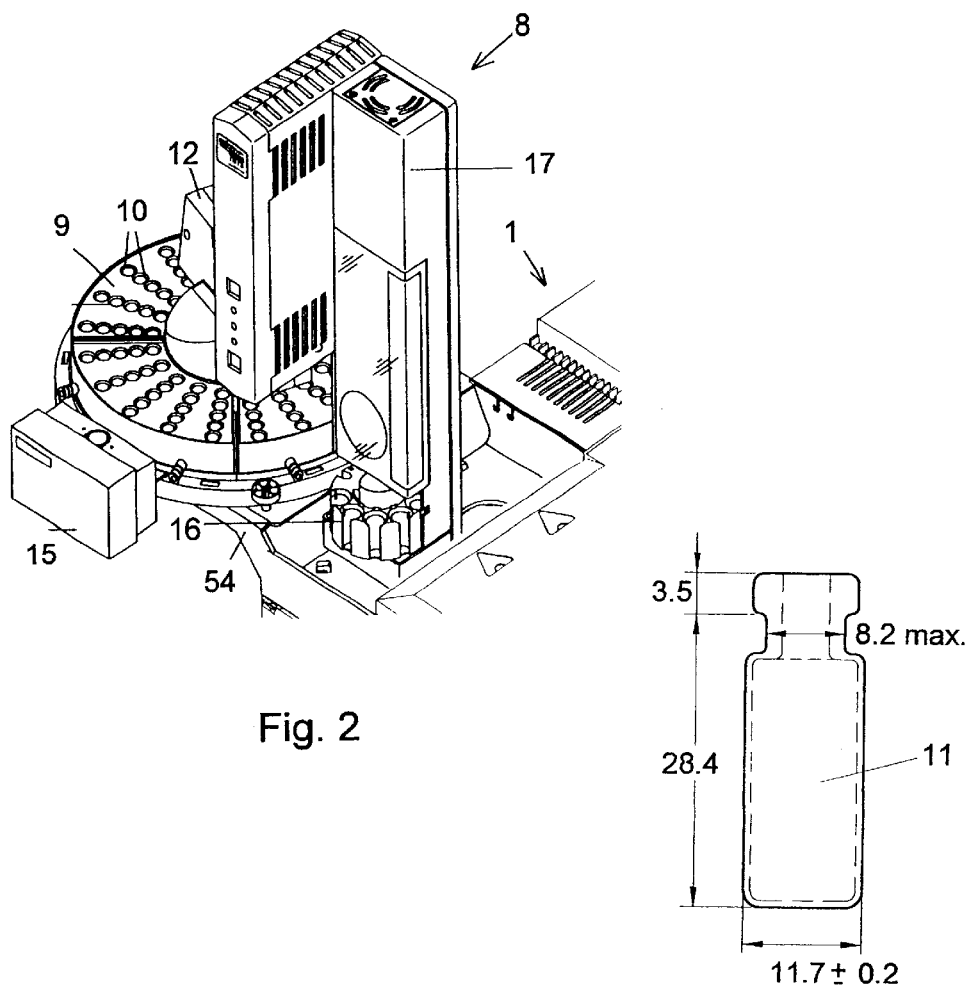
Fig. 2
Fig. 3
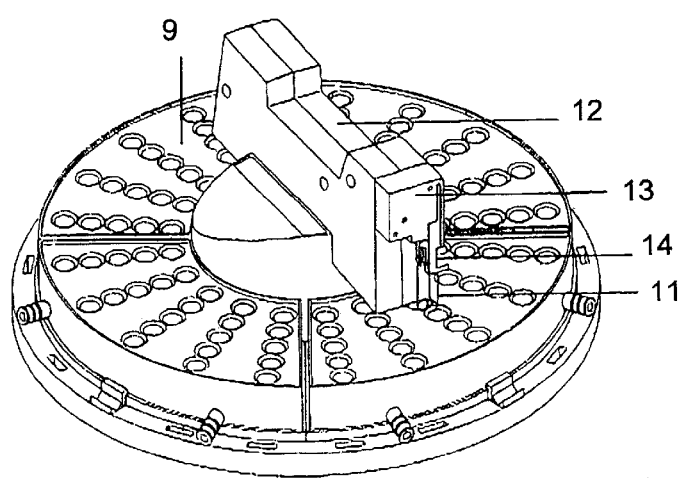
Fig. 4

ASSEMBLY FOR DESORBING SAMPLING TUBES; ADAPTER AND SAMPLING TUBES FOR SUCH AN ASSEMBLY; AND KIT OF PARTS FOR FORMING SUCH AN ASSEMBLY

This is a divisional of application Ser. No. 09/576,407, filed May 22, 2000.

It is well known to store samples of gases, liquids or like fluids in so-called sampling tubes. To that end, see, for instance, EP-A-0 816 823, the disclosure of which is to be considered inserted herein. Also solid substance in the form of granules or the like is stored in sampling tubes. Often, but not always, such sampling tubes are filled with absorption material in which the gas or the liquid, at least the substances present therein, are absorbed. Such sampling tubes are used, for instance, in surroundings where the danger exists that the atmosphere becomes contaminated, as in, for instance, laboratories, chemical factories, submarines and the like. Thus there are sampling tubes where the air to be measured is actively pumped through the sampling tube and where the sampling tube is therefore provided with an inflow opening and an outflow opening. When a sample of a gas to be sampled is being taken, the gas is pumped into the inflow opening, and the gas leaves the sampling tube via the outflow opening while leaving the substances contained in the gas behind in the absorption material. This procedure of sampling is designated as active sampling. Also known, from practice, is so-called passive sampling. In that case the sampling tubes have only one inflow opening during sampling. The air or the gas to be sampled diffuses via that opening into the absorption material while leaving the substances contained in the gas behind in the absorption material.

After some time has passed after sampling, the sampling tube is desorbed. To that end, heretofore, use has been made of special devices which are particularly costly. Desorption of the sampling tube occurs by heating the sampling tube, so that the substances present in the absorption material or in the solid substance contained in the sampling tube evaporate and are liberated. By blowing a carrier gas through the sampling tube during beating, the liberated substances are entrained by the carrier gas and can, for instance, be temporarily collected in a cold trap and subsequently be passed from the cold trap to a gas chromatograph in which the gases released can be analyzed. The known desorption devices are therefore provided with carrier gas supply means, heating means, a cold trap, control means for controlling the heating means and the like. This has as a result that the known desorption devices have a considerable cost price, which are of the order of a few tens of thousands of guilders.

The invention envisages an entirely new type of assembly by means of which sampling tubes can be desorbed, and which has a much lower cost price. Essentially, the invention is based on the insight that the gas chromatograph, which is necessary anyhow, essentially has all the means that are also used in a known desorption device. By means of the assembly, these means already present in the gas chromatograph are made available for desorbing sampling tubes.

To that end, the invention provides an assembly for desorbing sampling tubes, the assembly comprising a gas chromatograph known per se provided with an injector, the sampling tubes having an inflow opening and an outflow opening, the assembly comprising an adapter which is placed in the injector and which is provided with a chamber which is bounded by a heat conducting housing, the adapter being arranged for placing a sampling tube in the chamber thereof, while in a condition where a sampling tube is placed in the adapter, the inflow opening of the sampling tube is in fluid communication with a first carrier gas supply duct, while the outflow opening of the sampling tube is in fluid communication via the injector with a gas chromatography column contained in the gas chromatograph.

Due to the heat conducting housing of the adapter which bounds a chamber in which a sampling tube can be placed, it is possible by means of the heating means situated in the known injector of the known gas chromatograph, to heat a sampling tube placed in the chamber mentioned. Because moreover the inflow opening of the sampling tube is in fluid communication with a first carrier gas supply duct, and the outflow opening of the sampling tube is in fluid communication, via the injector, with a gas chromatography column contained in the gas chromatograph, substances located in the sampling tube that are liberated under the influence of the heating of the tube, can flow along with the carrier gas and be analyzed in the gas chromatography column. Since the known gas chromatograph has an extensive control by means of which the heating means of the injector can be accurately set, the temperature of the sampling tube contained in the chamber of the adapter can be accurately controlled, so that any particular temperature course of the sampling tube can be realized very accurately. Thus, for instance, first the light fractions contained in the sampling tube can be released by heating the sampling tube to, for instance, 50° C. for some time, whereafter subsequently heavier fractions can be liberated by heating the sampling tube to, for instance, 150°–250° C.

According to a further elaboration, it is particularly favorable when the adapter is provided with a heat conducting tube which is connected with the heat conducting housing, such that the tube and the housing are in heat exchange with each other, while the tube of the adapter, in the fitted condition of the adapter, reaches into the injector chamber. Because the tube reaches into the injector chamber, the heat transfer from the heating means of the injector will occur much more efficiently in that the tube of the adapter is directly surrounded by the heating means of the injector.

According to a further elaboration of the invention, it is particularly favorable when the sampling tubes have the shape of a vial known per se. When, according to a further elaboration of the invention, the assembly further comprises an autosampler known per se, which autosampler comprises a setup rack in which a number of vial-shaped sampling tubes can be set up, while the manipulator of the autosampler is arranged for picking up a sampling tube from the setup rack and placing such sampling tube in the adapter.

With such a device, without intervention of a laboratory worker, a large number of sampling tubes can be desorbed. Normally, the autosampler known per se is used to spout a liquid sample contained in a vial from this vial into the injector. The manipulator of the autosampler moves the vial in question from the setup rack into what is designated in practice by the term turret, from where an automatically operable spout sucks up the sample from the vial and then injects it into the injector of the gas chromatograph. As a result of the fact that the sampling tubes have the same shape as a vial known per se, the autosampler in most cases already present can be used for converting the gas chromatograph to a sampling tube desorbing device.

The invention also relates to an adapter evidently intended for use in an assembly according to the invention. Further, the invention relates to a sampling tube evidently intended for use in an assembly according to the invention.

Furthermore, the invention relates to a kit of parts comprising at least one adapter according to the invention, as well as a support for mounting an autosampler known per se on a gas chromatograph known per se, the support being designed such that the autosampler can place the sampling tubes in the adapter, which is placed in an injector of the gas chromatograph, without requiring adjustment of the control of the autosampler. It is then preferred when the kit also comprises various carrier gas ducts, at least one T-piece and a valve assembly.

The invention will be further elucidated with reference to the drawing, wherein

FIG. 2 shows a perspective view of an autosampler known per se of the firm Hewlett Packard®, which is mounted on the upper left corner of the gas chromatograph shown in FIG. 1;

FIG. 3 shows a side elevation of a vial known per se;

FIG. 4 shows a perspective view of a setup rack of an autosampler known per se with an associated manipulator;

Figure 1:
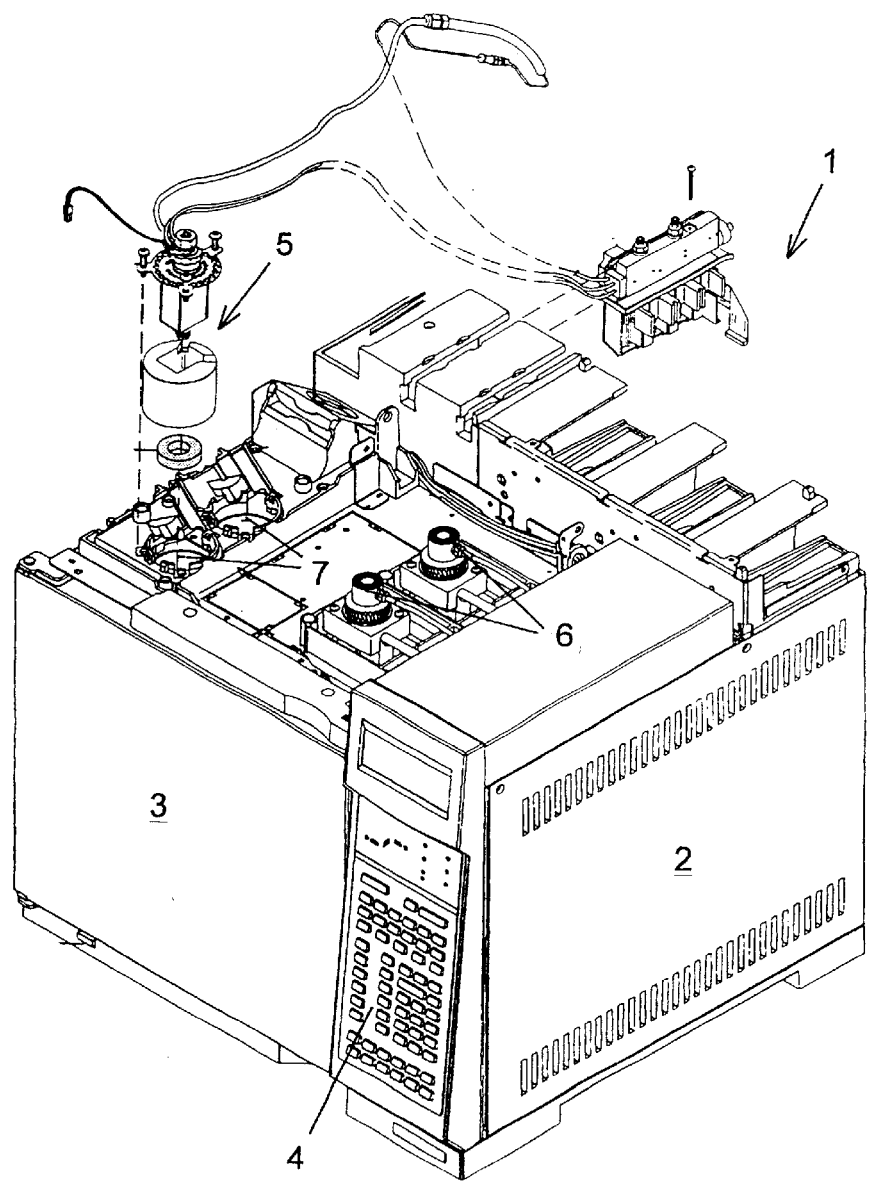
FIG. 1 shows a perspective view of a gas chromatograph known per se of the firm Hewlett Packard®, with a part of the top of the housing of the gas chromatograph broken away, and with the injector shown partly in exploded view.

The gas chromatograph represented in FIG. 1 is marketed by Hewlett Packard® and comprises a housing 2 in which an oven chamber is included which is closed off with an oven door 3. The housing 2 further contains a control which is operable by means of the control panel 4. In the oven chamber, in the present exemplary embodiment two, gas chromatography columns may be disposed, which are generally designed as capillary tubes provided with an internal coating. Such gas chromatography columns 42 are connected by an inlet end to a so-called injector 5 and by an outlet end to a so-called detector 6. In the exemplary embodiment shown, two detectors 6 are represented and two openings 7 in the top of the housing 2 for the purpose of injectors 5. The injectors 5 are provided with heating means in the form of a spiral filament which extends around an injector chamber into which normally the liquid to be analyzed is injected. Often injection occurs by means of a so-called autosampler which is mounted on the upper left corner of the gas chromatograph 1. Such an autosampler 8 is represented in perspective in FIG. 2 and comprises inter alia a setup rack 9 provided with a large number of openings 10 for receiving vials 11. A vial 11 is a vessel in which a liquid sample can be stored. By way of example, an exemplary embodiment of a vial 11 is represented in FIG. 3, with the specified dimensions being indicated in millimeters. The autosampler 8 further comprises an arm 12 which carries a gripper 13. The gripper 13 is provided with a gripper jaw 14 by means of which, in the use according to the prior art, vial 11 can be picked up from the tray 9. Optionally, the vial 11 can then be moved past a reader 15, so that a code carried by the vial can be read. The manipulator 12–14 of the autosampler 8, which manipulator comprises the arm 12, the gripper 13 and the gripper jaw 14, places a vial 11 taken from the setup rack 9, in the known use, in a so-called turret. This turret 16 is situated under a tower 17. Disposed in this tower 17 is an automatically energized injection needle by means of which liquid can be sucked up from a vial 11 which is disposed in the turret 16 and subsequently can be injected into the injector 5 of the gas chromatograph 1. The turret 16 mostly contains other liquid reservoirs with cleaning liquid for cleaning the injection needle after it has sucked up a sample from a vial 11 and delivered it to the injector 5. All devices discussed so far with reference to the drawings belong to the state of the art and are marketed inter alia by Hewlett Packard®.

Figure 5:
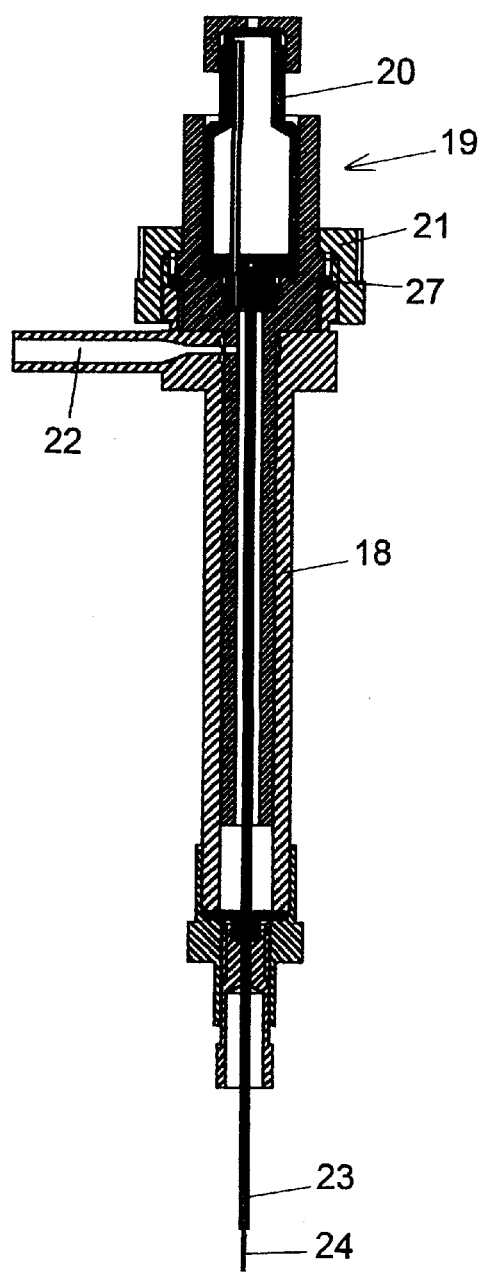
FIG. 5 shows a cross section of a part of the injector with an adapter placed therein and a sampling tube placed in the adapter.

FIG. 5 shows the housing 18, bounding the injector chamber, of the injector known per se. In this injector chamber, an adapter 19 is placed in which a sampling tube 20 is received. The adapter 19 is connected with the housing 18 of the injector chamber by means of a retaining nut 21, which housing 18 forms part of a standard injector. It is clearly visible that the housing 18 is provided with a so-called split-off channel 22 which is in fluid communication with the interior of the injector chamber. Further, a needle 23 is clearly shown, in which a capillary duct 24 extends as far as an outflow opening 25 of the sampling tube 20. An inflow opening 26 of the sampling tube 20 is in fluid communication with the injector chamber which is bounded by the housing 18.

For the purpose of a gas-tight closure adjacent the top of the injector chamber bounded by the injector housing 18, a sealing ring 27 is provided, which is clamped between the adapter 19 and the injector chamber housing 18.

Figure 6:
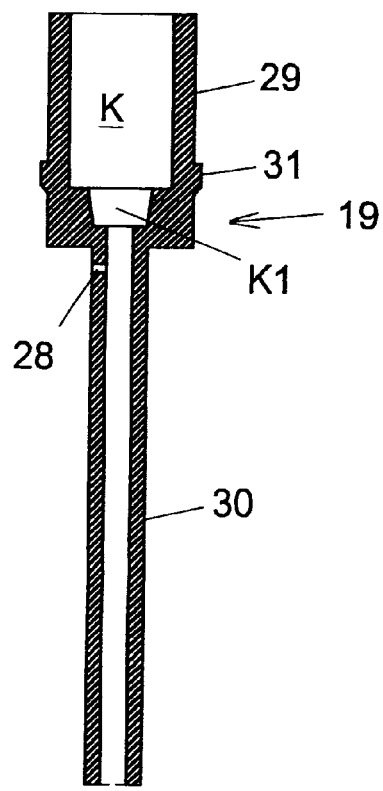
FIG. 6 shows a cross sectional view of the relevant parts of the adapter represented in FIG. 5.

FIG. 6, for the sake of clarity, shows the adapter 19, the fastening nut 21 and the sealing ring 27 in disassembled condition. The adapter 19 of the present exemplary embodiment comprises a chamber K which is bounded by a heat conducting housing 29. Further, the adapter 19 comprises a heat conducting tube 30 which is connected with the housing 29 such that they are in heat exchange with each other. In the present exemplary embodiment, the tube 30 and the housing 29 are constructed as a single integral part. Further, in the present exemplary embodiment, in the wall of the tube 30 a bore 28 is provided which, in the condition of the adapter 19 when fitted in the injector 18, is in fluid communication with the split-off channel 22 of the injector housing 18, as is clearly represented in FIG. 5. Although the heat conduction to the chamber K as a result of the presence of the heat conducting tube 30 is very good, it is also possible, according to an alternative elaboration of the invention, that the adapter is not provided with a heat conducting tube which reaches into the injection chamber bounded by the injector housing 18. To bring the temperature in the chamber K of the adapter to the desired value, it is then necessary that the heating means of the injector 5 are set at a higher temperature. It is self-explanatory that a design with heat conducting tube 30 is preferred. Further, the housing 29 of the adapter comprises a collar 31 which is engaged by the fastening nut 21 and against which the sealing ring 27 abuts when the adapter is mounted on the injector housing 18.

Figure 7:
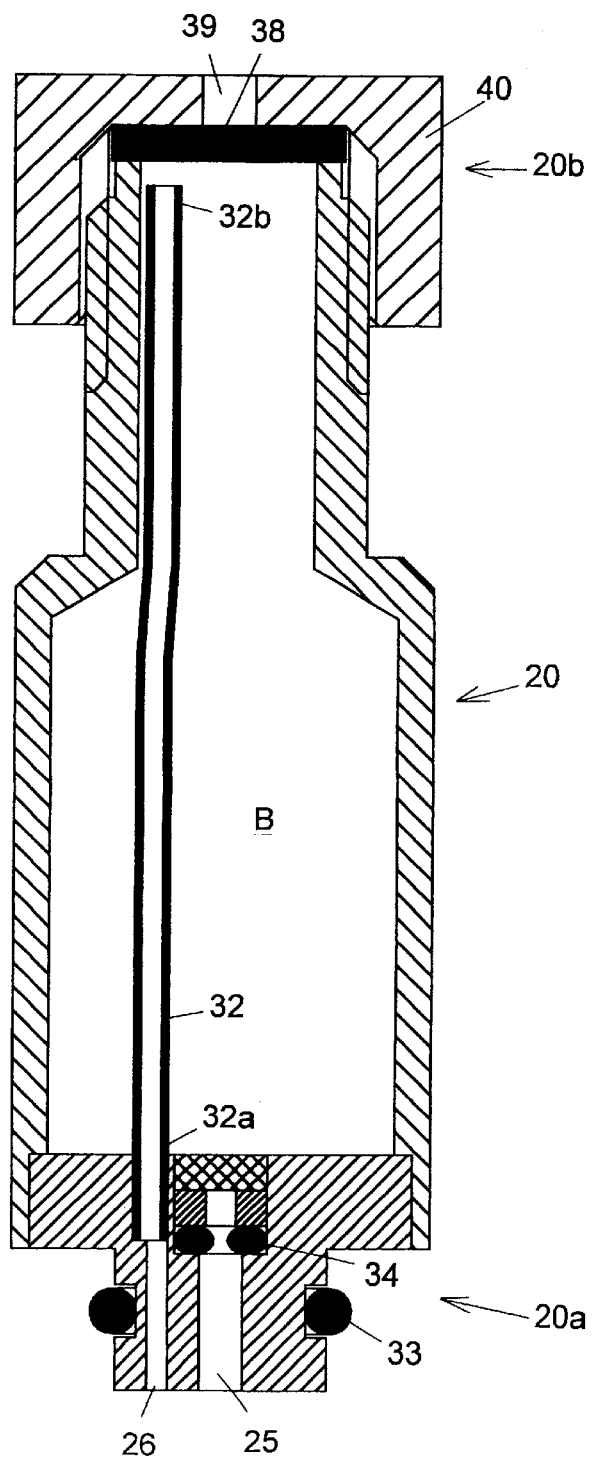
FIG. 7 shows a cross sectional view of a sampling tube that is represented in FIG. 5.
Figure 8:
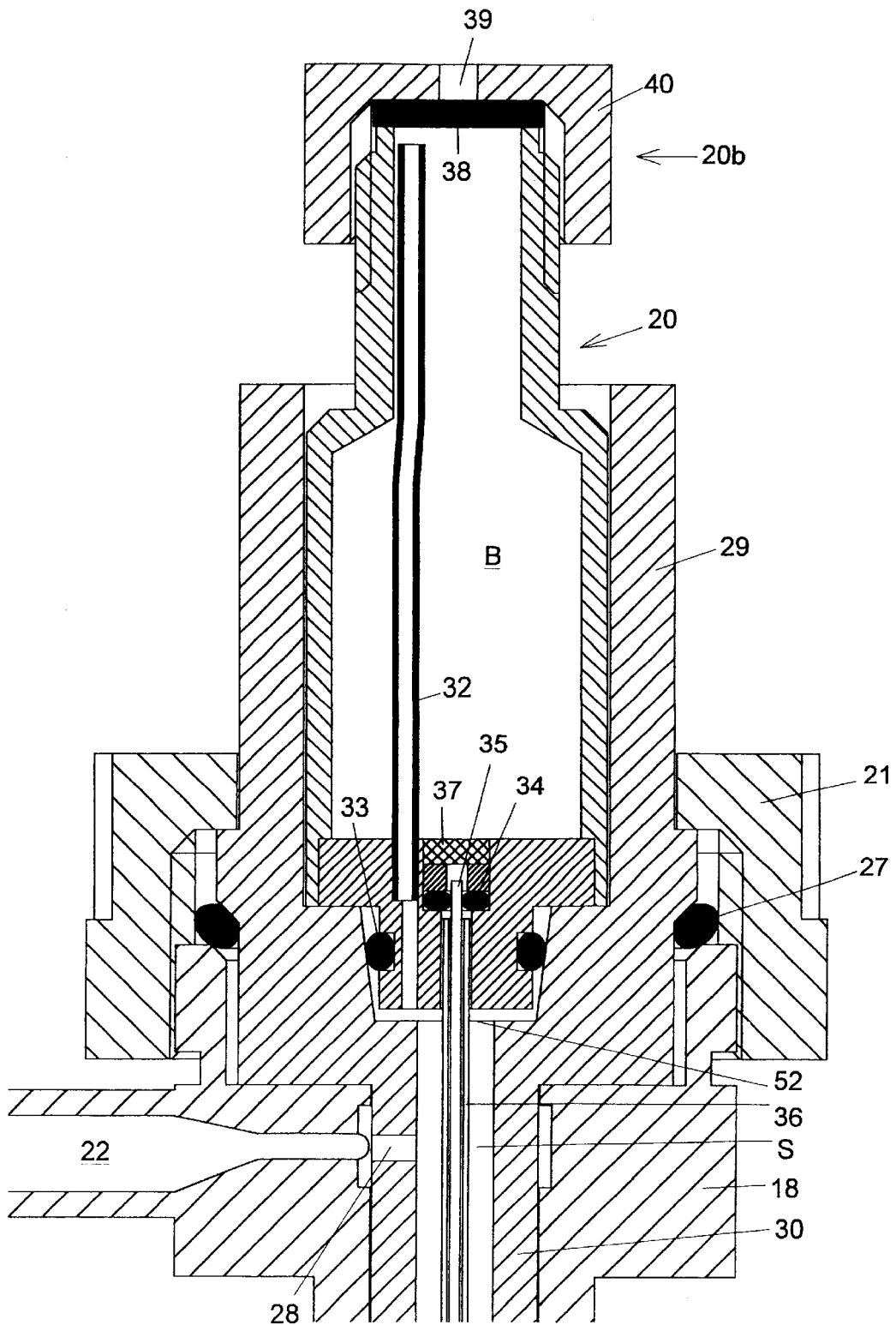
FIG. 8 shows in more detail how the adapter is mounted in the injector and the manner in which the inflow opening and the outflow opening of the sampling tube have been set into fluid communication with a carrier gas supply duct and a capillary, respectively.

FIG. 7 shows an exemplary embodiment of a sampling tube 20 which can be used in the adapter 19 which is represented in FIGS. 5 and 6. To enable the sampling tubes 20 to be automatically placed in the adapter 19 by means of the autosampler 8 from FIG. 2, the sampling tube 20 represented in FIG. 7 has substantially the same dimensions as the vial 1 which is represented in FIG. 3. Consequently, the sampling tubes 20 can be accommodated in the openings 10 of the setup rack 9 and be effectively engaged by the gripper 13 of the manipulator 12, 13, 14 of the autosampler 8 known per se. The sampling tube 20 which is represented in FIG. 7 is provided with an inflow opening 26 and an outflow opening which are provided at the same end 20a of the sampling tube 20. The sampling space B of the sampling tube 20 will generally contain an absorption material, such as, for instance, Tenax® (trademark of the firm Akzo; polyphenylene oxides). However, other absorption materials can also be selected, for instance activated carbon such as, for instance, carbograph™, carbosieve™ and carbotrap™ and other absorbing powders or granular materials such as silica gel, deactivated aluminum and the like. Further, it is possible that the chamber B of the sampling tube 20 is filled with a solid substance in granular form on which the measurement itself is to be performed, such as for instance a ground plastic or the like. Connected to the inflow opening 26 of the sampling tube 20 is a duct 32 having a first end 32a. The duct 32 extends through the inner chamber B of the sampling tube 20 and terminates through a second end 32b adjacent a second end 20b of the sampling tube, located opposite the first end 20a of the sampling tube. The first end 20a of the sampling tube 20 is provided with a first sealing ring 33 which is adapted for creating a fluid-tight seal between the tapering underside K1 of the chamber K of the adapter 19. Further, the end 20a of the sampling tube 20 is provided with a second sealing ring 34 which connects in a fluid-tight manner to a capillary 35 which is inserted into the outflow opening 25 of the sampling tube 20. FIG. 8 shows clearly the manner in which the sealing rings 33 and 34 cooperate respectively with the tapered underside K1 of the chamber K and a capillary column 35 reaching into the inflow opening. Further, it is clear from FIG. 8 in what way the fastening nut 21 secures the adapter 19 to the injector housing 18, with the sealing ring 27 forming a seal. Also visible is the bore 28 in the wall of the tube 30 of the adapter 19 and the manner in which it has been set in fluid communication with the split-off channel 22 of the injector. When the adapter 19 is mounted in the injector housing 18, a needle 36 reaches at least into the underside K1 of the chamber K of the adapter. This hollow needle 36 surrounds the capillary 35 which reaches slightly further into the chamber K of the adapter. When placing a sampling tube 20 in the adapter 19, the capillary 35 is automatically pushed beyond the sealing ring 34, so that a fluid communication between the capillary 35 and the inner chamber B of the sampling tube is effected. The inflow opening 26 of the sampling tube 20 is in fluid communication with the inner space S of the tube 30, which is fluid-tightly closed at the lower end, where it allows only the needle 36 and the capillary 35 to pass. In that way, therefore, a fluid communication is created between the inflow opening 26 and the split-off channel 22 of the injector 5. In the present exemplary embodiment, there is connected to the split-off channel 22 a carrier gas supply duct 41 with which carrier gas is supplied to the inner space S of the heat conducting tube 30. From this inner space S, the carrier gas flows to the inflow opening 26 of the sampling tube 20 and via the duct 32 to a second end 20b of the sampling tube. There the carrier gas flows into the inner chamber B of the sampling tube and there will have to penetrate through the absorption material to reach the outflow opening 25. The heating means of the injector chamber 5 are meanwhile heated up, so that the heat conducting tube 30 of the adapter 19 is heated. The heat in the heat conducting tube 30 is passed on to the heat conducting housing 29 bounding the chamber K of the adapter 19. Consequently, the sampling tube 20 will rise in temperature, so that the substances contained in the absorption material are liberated by evaporation and entrained with the carrier gas. To prevent the absorption material from ending up in the capillary 35, the needle 36 or the inner space S of the heat conducting tube 30, the absorption tube is provided with a screen 37 adjacent the outflow opening.

The sampling tube 20 represented in FIG. 7 is suitable for active sampling. To that end, a pump is connected to the first end 20a of the sampling tube 20, which pumps the gas to be sampled via the inflow opening 26 into the sampling tube 20 or sucks the gas to be sampled from the outflow opening 25 through the sampling tube 20. On the other hand, it is possible to use the sampling tube 20 for passive desorption. Then the first end 20a is closed off by means of a cap and the closing plate 38 is replaced with a screen. Via the opening 39 in the cover 40 of the sampling tube 20, the gas to be sampled can, by diffusion, diffuse into the interior B of the sampling tube 20. When the sampling tubes 20 are subsequently to be desorbed, the screen adjacent the second end 20b is replaced by a closing plate 38 and the cap which closes off the first end 20a of the sampling tube 20 is removed.

It is noted that the sampling tube 20 is preferably made of inert material, such as, for instance, glass, metal, ceramics, Teflon® (PTFE) or Vespel® (both trademarks of Dupont). To manufacture the sampling tube 20 in an economically advantageous manner, it can be manufactured from teflon by means of an injection molding process. Optionally, in the sampling tube in question, a transponder may be included in which an identification code and/or data about the sampling are stored. While the sampling tube is being placed from the setup rack 9 in the adapter 19, the transponder can be momentarily read in the reader 15 (see FIG. 2), so that the gas chromatograph 1 can run the correct program for desorbing the tube 20 in question.

Figure 9:
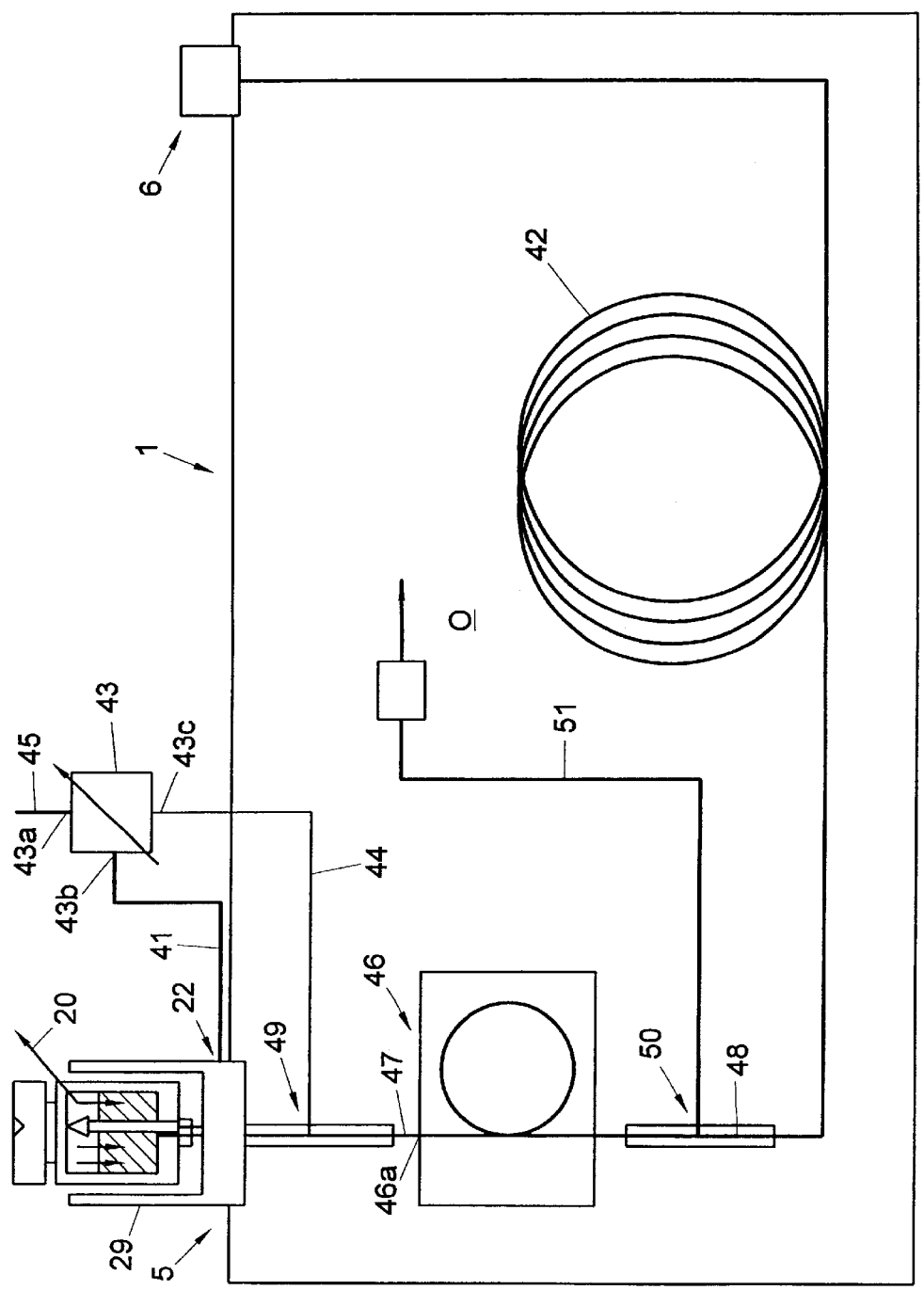
FIG. 9 shows a schematic view of an assembly according to the invention during the desorption of a sampling tube.
Figure 10:
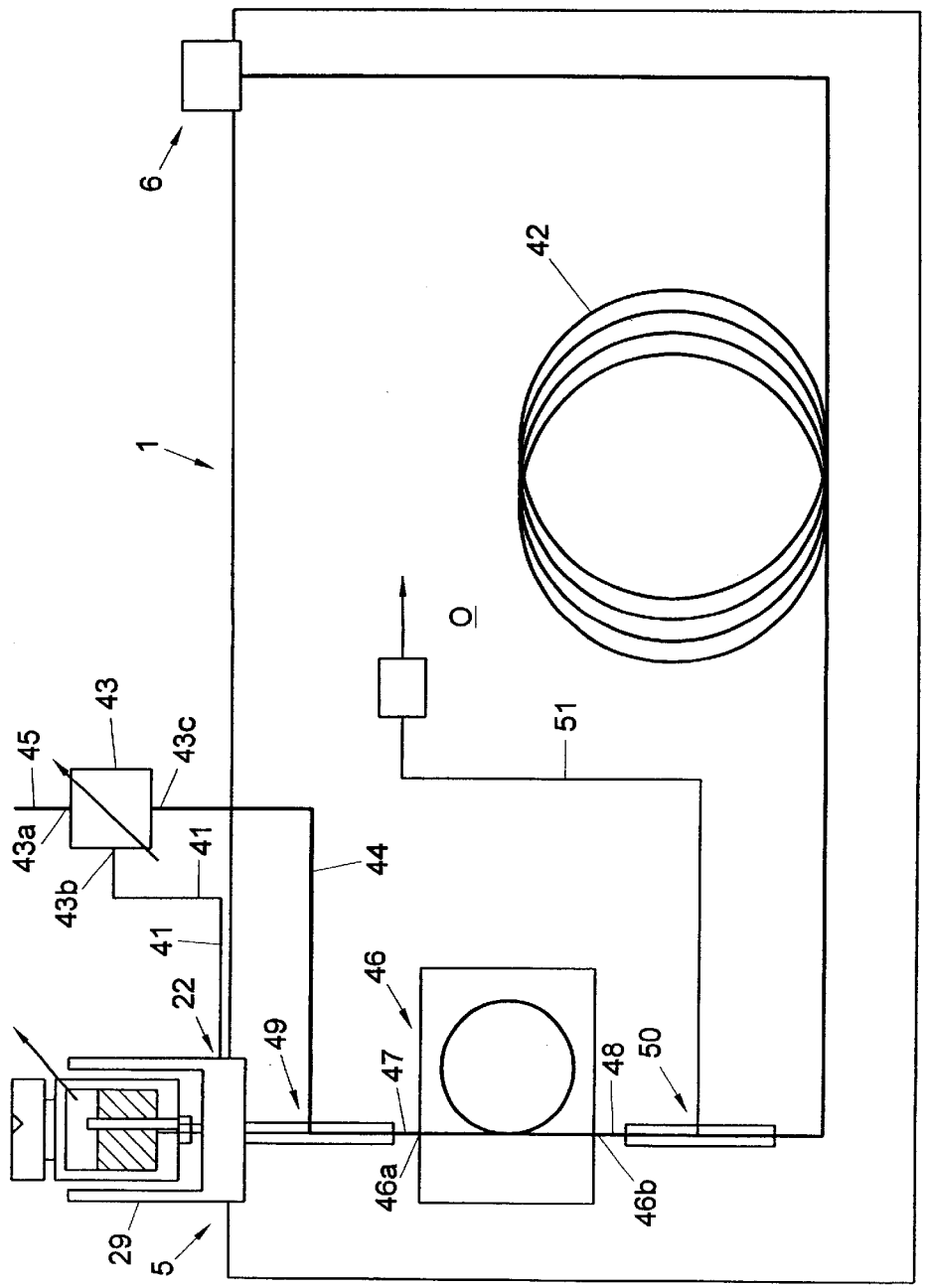
FIG. 10 shows a similar schematic representation to that represented in FIG. 9 during the analysis phase of a desorbed sampling tube.

FIGS. 9 and 10 show a schematic view of the assembly. FIG. 9 shows the desorption phase and FIG. 10 the analysis phase. FIGS. 9 and 10 schematically show the gas chromatograph 1 with the injector 5 on the left-hand side and the detector 6 on the right-hand side. The injector 5 and the detector 6 are in fluid communication with each other, inter alia via the gas chromatography column 42. In the injector 5, an adapter 19 as described hereinbefore is placed. In the chamber K of the adapter 19, a sampling tube 20 is placed. The inlet 26 of the sampling tube 20 in fluid communication with a first carrier gas duct 41 which is connected to the split-off channel 22 of the injector 5. The split-off channel 22 is also clearly represented in FIG. 5 and forms part of the injector housing 18. The other end of the first carrier gas supply duct 41 is connected with a first outlet 43b of a valve assembly 43, which in the present exemplary embodiment is designed as a three-way valve. The inlet 43a of the three-way valve 43 is connected with a carrier gas main supply duct 45. A second outlet 43c of the three-way valve 43 is connected to a second carrier gas supply duct 44. The three-way valve 43 sets the carrier gas main supply duct 45 in fluid communication with either the first carrier gas supply duct 41 or the second carrier gas supply duct 44. It is evident that the valve assembly 43 can also be designed as two single valves. The assembly further comprises a cold trap 46 which is arranged in the oven chamber O of the gas chromatograph 1. Such a cold trap 46 is formed by a capillary duct which is surrounded by a jacket, which jacket is cooled by means of, for instance, liquid nitrogen. As a result of the very low temperature prevailing in the cold trap 46, all substances desorbed from the sampling tube 20 will condense therein and be retained. As soon as the cooling of the cold trap 46 is switched off, and the capillary is heated up by means of the oven of the gas chromatograph 1, the substances condensed in the cold trap 46 will evaporate again and be liberated for analysis. The assembly further comprises a first connecting duct 47 which sets the capillary discharge 35 of the injector 5 in fluid communication with an inlet 46a of the cold trap 46. A second connecting duct 48 connects an outlet 46b of the cold trap 46 with the gas chromatography column 42. It is noted that the discharge 35, the first connecting duct 47, the cold trap 46 and the second connecting duct 48 are preferably designed as a capillary duct in which upstream and downstream of the cold trap, respectively, a first T-junction 49 and a second T-junction 50 are provided. Connected to the first T-junction 49 is an outlet of the second carrier gas supply duct 44, while a discharge duct 51 is connected to the second T-junction 50. The T-junctions 49, 50 can be designed in a variety of ways and are known per se.

During the desorption phase, which is represented in FIG. 9, the three-way valve 43 is set in a position such that the carrier gas main supply duct 45 is in fluid communication with the first carrier gas supply duct 41. The carrier gas flows via the split-off channel 22 of the injector 5 into the interior of the tube 30 of the adapter and from there via the inflow opening 26 of the sampling tube 20 and the duct 32 in the sampling tube 20 into the interior B of the sampling tube. The carrier gas proceeds to flow through the absorption material in the sampling tube 20 to the outflow opening 25 which is connected to the capillary 35 which forms the outlet or discharge of the injector. This capillary 35 leads to the first T-junction 49 and is in fluid communication with the first connecting duct 47 which leads to the cold trap 46. Because the adapter 19 is heated by the heating means of the injector 7, substances contained in the absorption material will be liberated and be entrained with the carrier gas passed through the sampling tube 20. This carrier gas flows to the cold trap 46 in which the substances condense from the carrier gas. As soon as the control of the gas chromatograph has determined that the desorption of the sampling tube 20 has taken place sufficiently long, the three-way valve 3 can be set in the second position, which is shown in FIG. 10. In this second position, the carrier gas main supply duct 45 is in fluid communication with the second carrier gas supply duct 44. The heating means of the injector 5 can be switched off since the desorption process has been completed and presently the analyzing process can take place. The cooling of the cold trap 46 can be switched off, so that the temperature in the cold trap 46 will rise rapidly to the temperature prevailing in the oven chamber O of the gas chromatograph 1. Preferably, the heat capacity of the cold trap is to be held low, for instance by designing the cold trap 46 as a capillary which is surrounded by a needle, through which needle liquid nitrogen can be passed. As soon as the temperature in the cold trap 46 rises, the substances condensed therein will start to evaporate and be entrained by the carrier gas which is supplied to the cold trap 46 via the second carrier gas supply duct 44 and the first T-junction 49 via the first connecting duct 47. From the cold trap 46 the carrier gas flows via the second connecting duct 48 to the second T-junction 50 to which an inlet of the gas chromatography column 42 is connected. At least a part of the carrier gas therefore flows through the gas chromatography column 42, where a separation of the substances occurs, so that they end up successively in the detector 6, on the basis of which it can be determined what substances were present in the absorption material of the sampling tube 20. By stepwise raising the temperature in the oven chamber O, first the light fractions can be liberated from the cold trap 46 and then the heavier fractions.

Hereinabove, a sampling tube 20 has been discussed in which the inflow opening 26 and the outflow opening 25 are situated at a first end 20a of the sampling tube 20. This has as an advantage that, when placing the sampling tube 20, in a very simple manner both the inflow opening 26 and the outflow opening 25 can be set in fluid communication with a carrier gas supply duct 41 and the gas chromatography column 42, respectively. It is also possible, however, according to an alternative further elaboration of the invention, that the sampling tube 120 is provided with an inflow opening 126 on a second end 120b and an outflow opening 125 on a first end 120a of the sampling tube 120. It is then necessary, however, that the assembly is provided with a movable first carrier gas supply duct 141 of which an outflow opening 141a is adapted to be connectable to the inflow opening 126 of the sampling tube 120. In a wall of the housing 29 of the chamber K of the adapter 19 a discharge 35 is provided which, in the condition of the sampling tube 20 when placed in the chamber K, connects to the outflow opening 125 of the sampling tube 120. In the exemplary embodiment represented in FIGS. 11 and 12, the movable carrier gas supply duct 141 is included in a swiveling arm 53. The swiveling arm 53 is provided with a carrying cam 154 which, as the sampling tube 120 is fitted, is engaged by the lower edge of the cover 140 of the sampling tube 120. With this engagement, the swiveling arm 53 gradually swivels along with the movement of the sampling tube 120, while simultaneously the outflow opening 141a of the first carrier gas supply duct 141 is pushed into the inflow opening 126 of the sampling tube 120.

Figure 11:
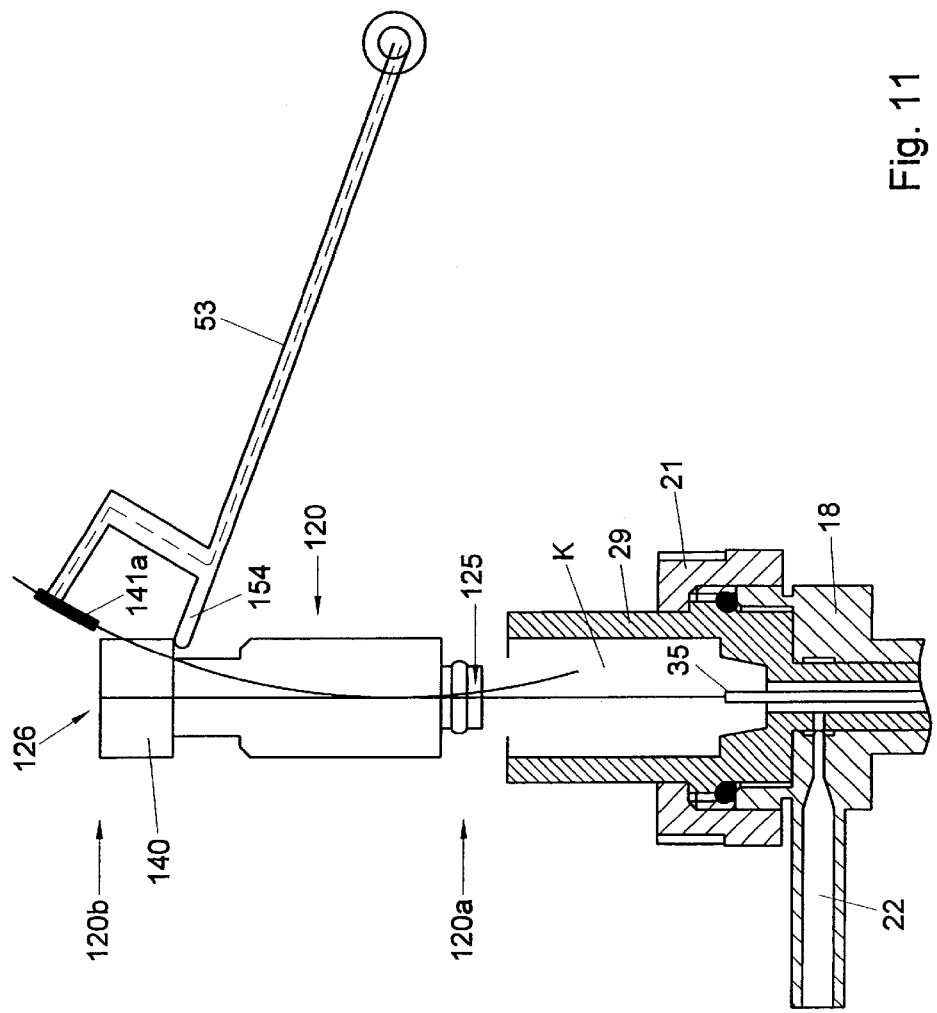
FIG. 11 shows a sampling tube of alternative design with a carrier gas supply duct which is included in a swiveling arm.
Figure 12:
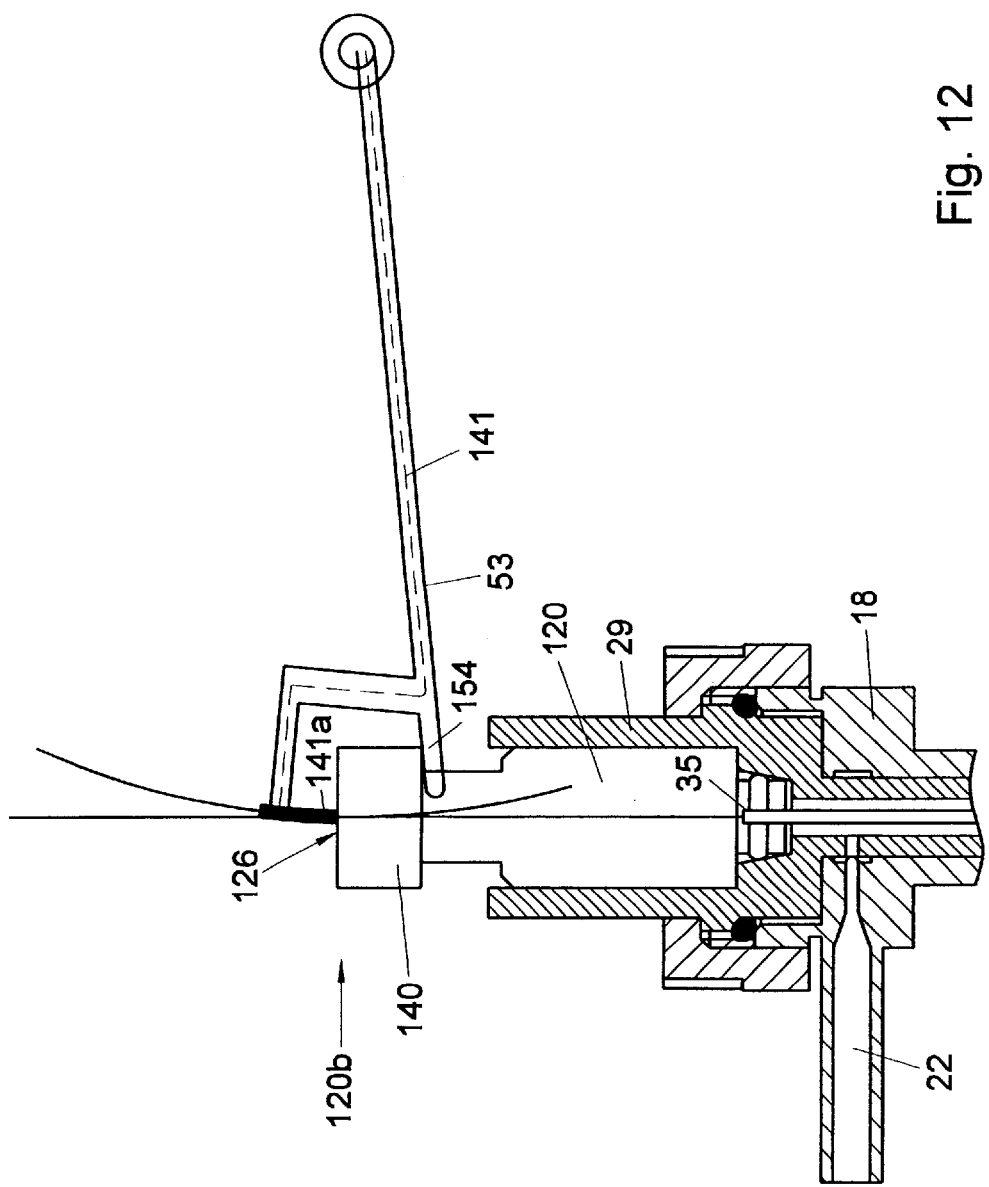
FIG. 12 shows a similar view to that represented in FIG. 10, where the swivel arm has taken a second position.

FIG. 11 shows a position of the sampling tube 20 and the swiveling arm 53 at the beginning of the engagement and FIG. 12 shows the swiveling arm 53 and the sampling tube 120 in a condition in which the sampling tube 120 is disposed in the chamber K of the adapter 19. Clearly visible is that the outflow opening 141a of the first carrier gas supply duct 141 has been set to connect to the inflow opening 126 of the sampling tube 120. Further, it is clearly visible that the discharge 35 has been set into fluid communication with the outflow opening 125 of the sampling tube 120.

It will be clear that the invention is not limited to the exemplary embodiments described but that various modifications within the scope of the invention are possible. Essential is that as a result of the presence of the adapter which has been placed in the injector, a gas chromatograph known per se can be used as desorption device for sampling tubes.

The fact that from the outflow opening 25 of the desorption tube the capillary 35 and the first connecting duct 47 as far as the cold trap 46 are wholly heated—since they are disposed in the oven chamber 0 of the gas chromatograph 1—precludes desorbed substances precipitating on these duct parts before they reach the cold trap 46. This provides the advantage that no substances that were present in the sampling tube are lost during the desorption process. The accuracy of the measurement taking place in the gas chromatograph is thereby influenced in a positive way. In the known desorption devices which are arranged separately from the gas chromatograph, this danger is definitely present. Not only is the known desorption device much more costly than is the proposal according to the invention, but also the accuracy of the known device is lesser than that of the proposal according to the invention.

What is claimed is:

1. An assembly for desorbing sampling tubes (20), the assembly comprising a gas chromatograph (1) known per se provided with an injector (5), the sampling tubes (20) being provided with an inflow opening (26) and an outflow opening (25), the assembly comprising an adapter (19) which is placed in the injector (5) and which is provided with an adapter chamber (K) which is bounded by a heat conducting housing (29), the adapter (19) being arranged for placing a sampling tube (20) in the adapter chamber (K) thereof, while in a mounted condition of a sampling tube (20) wherein it is placed in the adapter (19), the inflow opening (26) thereof is in fluid communication with a first carrier gas supply duct (41), while the outflow opening (25) of the sampling tube (20) is in fluid communication via the injector (5) with a gas chromatography column (42) disposed in the gas chromatograph (1), the assembly further comprising an autosampler (8) known per se, which autosampler (8) comprises a setup rack (10) in which a of sampling tubes can be set up, while a manipulator (12, 13, 14) of the autosampler (8) is adapted for picking up a sampling tube (20, 120) the setup rack (10) and placing such a sampling tube (20, 120) in the adapter.

2. An, assembly according to claim 1, characterized in that the injector (5) comprises a split-off channel (22), the first carrier gas supply duct (41) being connected to the split-off channel (22) in the manner of a T-junction.

3. An assembly according to claim 1, characterized in that the sampling tubes (20) used therein are provided with an inflow opening (26) and an outflow opening (25) which are situated on the same end (20a) of the sampling tube (20), while in a wall of the housing (29) of the chamber (K) of the adapter (19(both a supply (52) and a discharge (35) are provided which, in a condition of the sampling tube (20) when placed in the chamber (K), connect to, respectively, the inflow opening (26) and the outflow opening (25) of the sampling tube (20).

4. An assembly according to claim 1, characterized in that the sampling tubes (120) used therein are provided with an inflow opening (126) on a second end (120b) and an outflow opening (125) on a first end (120a) of the sampling tube (120), the assembly comprising a displaceable first carrier gas supply duct (141) of which an outflow opening (141a) is adapted to be connectable with the inflow opening of the sampling tube (120), while in a wall of the housing (29) of the chamber (K) of the adapter (19) a discharge (35) is provided which, in a condition of a sampling tube (120) when placed in the chamber, connects to the outflow opening (125) of the sampling tube (120).

5. An assembly according to claim 4, characterized in that the displaceable first carrier gas supply duct (141) extends in a swiveling arm (53).

6. An assembly according to claim 1, characterized in that the sampling tube (20, 120) has the shape of a vial known per se.

7. An assembly according to claim 1, characterized in that (a) sampling tube (20, 120) has the shape of a vial known per se, (b) the assembly further comprises an autosampler (8) known per se, which autosampler (8) comprises a setup rack (10) in which a number of sampling tubes (20, 120) can be set up, while a manipulator (12, 13, 14) of the autosampler (8) is adapted for picking up a sampling tube (20, 120) from the setup rack (10) and placing such a sampling tube (20, 120) in the adapter (19) and (c) said autosampler (8) is mounted on a base (54) which is connected with a housing of the gas chromatograph (1).

8. An assembly according to claim 1, characterized in that (a) the sampling tube (20, 120) has the shape of a vial known per se, (b) the assembly further comprises an autosampler (8) known per se, which autosampler (8) comprises a setup rack (10) in which a number of sampling tubes (20, 120) can be set up, while a manipulator (12, 13, 14) of the autosampler (8) is adapted for picking up a sampling tube (20, 120) from the setup rack (10) and placing such a sampling tube (20, 120) in the adapter (19), and (c) the chromatograph (1) comprises two injectors (7), while in each injector (5) an adapter (19) is arranged, the autosampler (8) being arranged for placing a sampling tube (20, 120) in both the one and the other adapter (19).

9. An adapter comprising an assembly according to claim 1, characterized in that (a) the adapter comprises a heat conducting housing (29) which bounds a chamber (K), the adapter (19) further comprising a heat conducting tube (30) which is connected with the housing (29) such that they are in heat exchange with each other, and (b) the housing (20) and the tube (30) are constructed as a single part.

10. An adapter for use in the assembly of claim 1, characterized in that said adapter comprises a heat conducting housing (29) which bounds a chamber (K), the adapter (19) further comprising a heat conducting tube (30) which is connected with the housing (29) such that they are in heat exchange with each other.

11. An adapter according to claim 10 characterized in that in the wall of the tube (30) a bore (28) is provided which, in a mounted condition of the adapter (19) in the injector (5) is in fluid communication with the split-off channel (22) of the injector (5).

12. A sampling tube comprising an assembly according to claim 1, characterized in that the sampling tube (20, 120) is filled with an adsorption material.

13. A sampling tube according to claim 12, characterized in that the sampling tube (20, 120) has the form of a vial known per se.

14. A sampling tube according to claim 12 characterized in that the sampling tube (20, 120) is provided with a transponder.

15. A sampling tube according to claim 12, characterized by an inflow opening (26) and an outflow opening (25) which are situated at a first end (20a) of the sampling tube (20), while in the interior (B) of the sampling tube (20) a duct (32) extends which is connected by a first end (32a) to the inflow opening (26) and which terminates by a second end (32b) in the interior (B) of the sampling tube (20) adjacent a second end (20b) of the sampling tube (20), situated opposite the first end (20a) of the sampling tube (20).

16. A sampling tube according to claim 12, characterized in that the sampling tube (20) is manufactured from an inert material.

17. A sampling tube according to claim 12, characterized in that the sampling tube (20) is manufactured from an inert material, characterized in that it has been manufactured from TEFLON® by means of an injection molding process.

18. A kit, comprising at least one adapter (19) according to claim 10, as well as a support (54) for mounting an autosampler (8) known per se on a gas chromatograph (1) known per se, the support (54) being so designed that the autosampler (8) is capable of placing the sampling tubes (20, 120) in the adapter (19) which as been placed in an injector (5) of the gas chromatograph (1), without requiring adjustment of the control of the autosampler (8).

19. A kit according to claim 18, further comprising various carrier gas ducts (41, 44, 45), at least one T-piece (49, 50) for forming a T-junction as described in claim 2 and a valve assembly (43).

* * * * *

UNITED STATES PATENT AND TRADEMARK OFFICE
CERTIFICATE OF CORRECTION

PATENT NO. : 6,662,626 B2
DATED : December 16, 2003
INVENTOR(S) : Marinus Frans van der Maas It is certified that error appears in the above-identified patent and that said Letters Patent is hereby corrected as shown below:

Column 1,
Line 42, "beating" should read -- heating --; and

Column 8,
Line 60, "0" should read -- O --.

Signed and Sealed this

Second Day of November, 2004

JON W. DUDAS
*Director of the United States Patent and Trademark Office*